(12) United States Patent
Schiødt et al.

(10) Patent No.: US 6,441,230 B1
(45) Date of Patent: Aug. 27, 2002

(54) TRIPHOS POLYMER COMPOUNDS AND ACYLATION AGENT USEFUL IN THEIR PREPARATION

(75) Inventors: Niels Christian Schiødt, Brønshøj; Finn Joensen, Hørsholm, both of (DK)

(73) Assignee: Haldor Topsoe A/S, Lyngby (DK)

( * ) Notice: Subject to any disclaimer, the term of this patent is extended or adjusted under 35 U.S.C. 154(b) by 0 days.

(21) Appl. No.: 09/781,356

(22) Filed: Feb. 12, 2001

Related U.S. Application Data

(63) Continuation-in-part of application No. 09/459,533, filed on Dec. 13, 1999, now abandoned, and a continuation-in-part of application No. 09/459,534, filed on Dec. 13, 1999, now abandoned.

(60) Provisional application No. 60/113,869, filed on Dec. 23, 1998, and provisional application No. 60/113,868, filed on Dec. 23, 1998.

(51) Int. Cl.$^7$ ............................................. C07C 309/00
(52) U.S. Cl. ....................................................... 562/879
(58) Field of Search ........................................ 562/879

(56) References Cited

U.S. PATENT DOCUMENTS 3,737,447 A * 6/1973 Mazur ........................ 260/456

OTHER PUBLICATIONS

Effenberger et al (1996): J. Am. Chem. Soc. vol. 118, 12572–12579.*

Chemical Abstracts, vol. 55, No. 1503f; Kravets, V.P. Zhur. Vsesoyuz Khim. Obshchestva im. D.I. Mendeleeva 5; (1960), pp. 479–480.

Kravets, V.P. Zhur. Vsesoyuz Khim. Obshchestva im. D.I. Mendeleeva 5; (1960), pp. 479–480.

STN International, CAPLUS Database, Chemical Abstracts Service, (Columbus, Ohio), No. 1987: 422927 (1987).

STN International, CAPLUS Database, Chemical Abstracts Service, (Columbus, Ohio), No. 1981: 120812 (1981).

STN International, CAOLD Database, Chemical Abstracts Service, (Columbus, Ohio), No. CA54:382d (1960).

STN International, CAOLD Database, Chemical Abstracts Service, (Columbus, Ohio), No. CA53:21774 (1959).

* cited by examiner

*Primary Examiner*—Floyd D. Higel
*Assistant Examiner*—Golam M. M. Shameem
(74) *Attorney, Agent, or Firm*—Dickstein Shapiro Morin & Oshinsky

(57) ABSTRACT

Material and process of preparing such material, of the formula

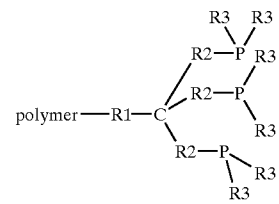

where $R_1$ is a linker and $C(R^2P(R^3)_2)_3$ group is a triphos moiety; and wherein $R^1$ is selected from branched and linear alkyl group and alkyl carbonyl group optionally substituted with functional groups comprising carbonyl, alkoxy, hydroxy, amino, nitro, carboxylic or sulfonic acid and esters or amides thereof; $R^2$ are methylene ($CH_2$) or substituted methylene groups; $R^3$ are linear or branched alkyl or phenyl or substituted phenyl groups; polymer is any polymer containing aromatic groups, comprising polystyrene, poly-vinyl pyridine, poly pyrrole, poly pyrrolidone or derivatives thereof. The material impregnated with a transition metal has catalytic properties. The preparation of the material involves the use of an acylating agent having the formula $CF_3SO_3C(O)C(H_2X)_3$ or an anhydride thereof, where X is a halogen.

3 Claims, No Drawings

TRIPHOS POLYMER COMPOUNDS AND ACYLATION AGENT USEFUL IN THEIR PREPARATION

This is a continuation in part of applications Ser. Nos. 09/459,533 and 09/459,534, both filed on Dec. 13, 1999, which applications claim the benefit of U.S. Provisional Application Serial No. 60/113,869 and 60/113,868, both filed Dec. 23, 1998, respectively.

BACKGROUND OF THE INVENTION

The present invention relates to previously unknown polymeric materials with tripodal chelating tris (diphenylphosphinomethyl)methyl groups covalently bound to surface of a polymer. These polymeric materials are easily impregnated with transition metals, after which they may serve as immobilized molecular catalysts with respect to a variety of reactions. A feature of the invention relates to a novel acylation agent useful in preparing these polymeric materials.

It is well known that the role of a catalyst is to increase the rate and selectivity of a chemical reaction. Such catalyst may be heterogeneous (insoluble in the reaction medium) or homogeneous (soluble). Each kind has some advantages and some drawbacks. The homogeneous catalysts are often well defined transition metal complexes with a high selectivity, but the separation of the catalyst from the product imposes an inherent problem. Therefore, it is desirable to immobilize such homogeneous catalysts on an insoluble support.

The homogeneous catalysts are typically transition metal complexes consisting of a transition metal ion and some ligands. Phosphine ligands are among the most common, as e.g. in the Rhone-Poulenc hydroformylation process (B. Cornils and E. Wiebus chemtech 25, 33, 1995). Phosphine ligands are furthermore suitable for covalent immobilization and phosphine-modified supports have been well known for year (G. O. Evans, C. U. Pittman Jr., R. McMillan, R. T. Beach and R. Jones J. Organomet. Chem. 67, 295, 1974; K. G. Allum, R. D. Hancock, I. V. Howell, R. C. Pitkethly and P. J. Robinson Jones J. Organomet. Chem. 87, 189, 1975).

During the past two decades, transition metal complexes of the tridentate phosphine ligand 1,1,1-tris (diphenylphosphinomethyl)ethane (commonly called triphos) have attracted increasing attention within the field of homogeneous catalysis. Thus, it has been reported that a rhodium complex with triphos is an active hydroformylation catalyst (C. Bianchini, A. Meli, M. Peruzzini, F. Vizza, P. Frediani and J. A. Ramirez Organometallics 9, 226, 1990), and a very thorough study of hydrodesulfurisation by rhodium, iridium and ruthenium complexes with triphos has been published (C. Bianchini and A. Meli in T. Weber et al. (eds.) Transition Metal Sulphides, Kluwer Academic Publishers, 1998).

It has been found that by swelling material based on a polymer resin with covalently bound triphos-type groups in a solution containing suitable transition metal salts or complexes, the metal ions are captured by the resin-bound triphos ligands. Thus, the immobilized triphos complexes are catalytically active at different reactions.

SUMMARY OF THE INVENTION

The invention provides materials, which generally are characterized by the following three parts:

polymer-linker-triphos represented by the general chemical formula:

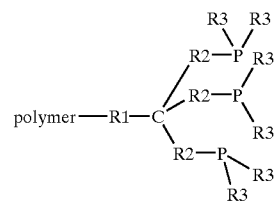

where $R^1$ is the linker and the $C(R^2P(R^3)_2)_3$ group is the triphos part.

$R^1$ is selected from branched and linear alkyl group and alkyl carbonyl group optionally substituted with functional groups comprising carbonyl, alkoxy, hydroxy, amino, nitro, carboxylic or sulfonic acid and esters or amides thereof.

$R^2$ are methylene ($CH_2$) or substituted methylene groups.

$R_3$ are linear or branched alkyl or phenyl or substituted phenyl groups.

The polymer may be any polymer containing aromatic groups, such as polystyrene, poly vinyl pyridine, poly pyrrole, poly pyrrolidone or derivatives thereof, such as the said polymers substituted with one or more alkyl, formyl, alkyl carbonyl, alkoxy, hydroxy, amino, nitro or carboxylic or sulfonic acid and esters or amides thereof in the aromatic ring. The polymer may also be a copolymer, e.g. a grafted polymer or block-copolymer as long as aromatic groups are present for functionalization with the triphos ligand moiety.

The linker-triphos groups are covalently bound to the phenyl groups of the polymer, thus providing immobilized sites for chelations of transition metal ions.

The polymer is reacted with a novel acylating agent, 1,1,1-tris(halomethane)acetyl trifluoromethanesulphonate or an anhydride thereof whereby the 1,1,1-tris(halomethyl) acetyl group is attached to the benzene nuclei. The resulting acylated product is then recited with lithium diphenylphosphide to produce a polymer-linker-triphos of this invention. The latter material is then impregnated with a transition metal. The impregnated product has catalytic properties and may be used to catalyze the carbonylation of methanol, the hydrodesulphurization is of sulphur containing compounds and the hydroformylation of olefines.

The novel acylating agent referred to above is prepared by reacting a tris(halomethyl)acetyl halide with trifluoromethanesulphonic acid or a salt thereof.

The following examples are illustrative of the invention.

EXAMPLE 1

Preparation of polymer carrier.

Two polymers were used for the preparation of the materials described here. PEPS, which is polystyrene (PS) grafted on the surface of polyethylene (PE) was prepared as follows: Polyethylene grains (0.2–0.4 mm) were crossbound by irradiation in an electron accelerator facility with a dose of 298 kGy. The crossbound PE was then immersed in a solution of styrene in methanol (30% v/v styrene) and submitted to y-irradiation from a $^{60}$Co source with a dose of 25 kGy. The material was washed thoroughly with methanol and with dichloromethane. It was then dried in a vacuum oven at 40° C. for at least 8 hours. The material thus obtained contains 34.2% by weight polystyrene. The triphos-derived resin based on PEPS is called I (see the synthesis scheme below).

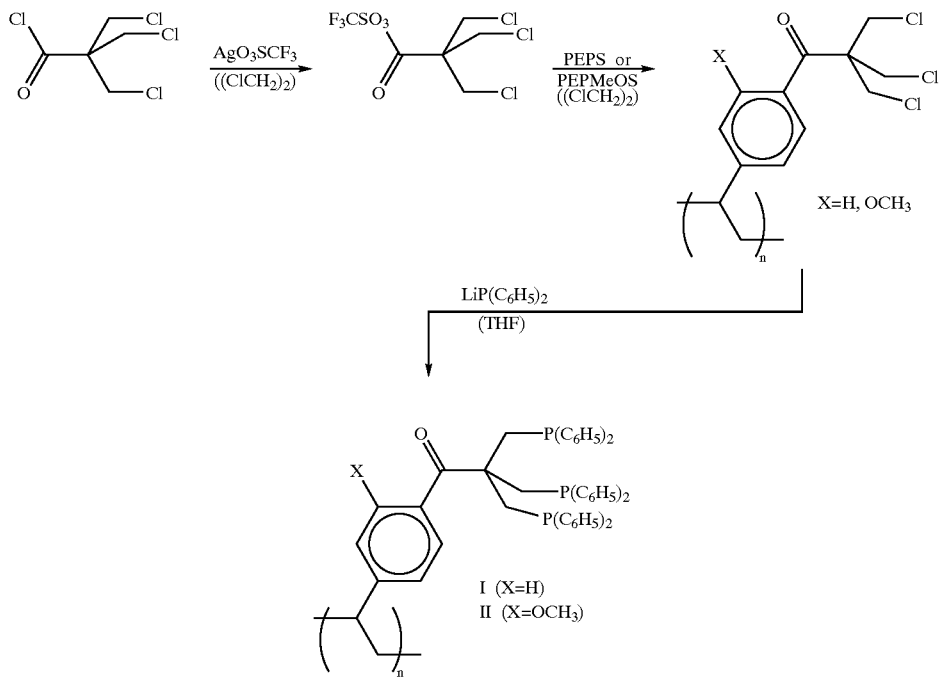

Using a commercial polymer such as PS crossbound with divinylbenzene could give rise to a material similar to I with respect to chemical properties, but with better thermal and mechanical properties.

EXAMPLE 2

Preparation of polymer carrier.

The other polymer PEPMeOS was prepared in exactly the same manner, but with 3-methoxystyrene instead of styrene. This gave rise to a material containing 35.6% poly (3-methoxy)styrene. The triphos-derived resin based on PEPMeOS is called II.

EXAMPLE 3

Functionalization of polymer carrier.

Tris (chloromethyl) acetyl chloride $(ClCH_2)_3CCOCl$ (66.80 g; 0.30 mole) was dissolved in 1,2-dichloroethane (300 ml) at and stirred magnetically with an equimolar amount of solid silver trifluoromethanesulphonate (62.00 g; 0.24 mole) at room temperature for 24 hours in a dry atmosphere in the dark. This caused the formation of an almost quantitative precipitate of silver chloride, which was filtered off in a dry atmosphere and with dry equipment. The filtrate containing the mixed carboxylic acid trifluoromethanesulphonic acid anhydride was then used for the acylation of the polymer. The polymer (PEPS) in the form of small grains (100 g; equivalent to 34.2 g PS; 0.33 mole) were added to the filtrate. An additional 400 ml 1,2-dichloroethane were added and the temperature was raised to the boiling point of the solvent and kept there for 3 hours. After having cooled the reaction flask to room temperature, the polymer was washed with 1,2-dichloroethane and then within heptane and dried until constant weight was achieved.

The acylated polymer was converted to I by treatment with a solution of lithium diphenylphosphide in tetrahydrofuran (THF) prepared according to literature methods (G. Kordosky, B. R. Cook, J. Cloyd Jr., and D. W. Meek Inorg. Synth. Coll. Vol. XIV, 14, 1973). All operations involving diphenylphosphide anion as well as the product polymer I were conducted in an argon atmosphere to prevent oxidation. The best results were obtained by cooling the lithium diphenylphosphide solution (0.25 mole) to −78° C., adding the thoroughly dried polymer (containing approximately 0,075 mole Cl) in one portion and allowing the slurry (magnetically stirred) to warm up to room temperature within one hour and subsequent refluxing the slurry for 2 hours. Then the excess diphenylphosphide was destroyed by the addition of acetic acid (6 g) followed by the addition of 100 ml ethanol. The polymer was filtered off and washed with 250 ml of each of the following solvents: Ethanol, water, acetone (twice), benzene and light petroleum ether. The polymer was dried in a vacuum oven at 40° C.

Preparation of Transition Metal Impregnated I and II

EXAMPLE 4A

Preparation of rhodium impregnated I (I-Rh).

A stream of CO was led through 50 ml of toluene for 20 minutes at room temperature. While maintaining a slow stream of CO, $Rh_2Cl_2(CO)_4$ (1.5 g) were dissolved in the toluene. A sample of I (10 g) was added to the yellow solution, causing a vigorous evolution of CO (bubbles). Within 15 minutes, the polymer had turned red while the color of the solution had fainted. The slurry was stirred for a further 4 hours. The polymer was then filtered off, washed with toluene until the washings were completely colorless and then with petroleum ether. The polymer was dried overnight in a stream of CO. Weight: 10.80 g.

EXAMPLE 4B

Preparation of rhodium impregnated II (II-Rh).

This material was prepared in the same way as I-Rh. From 8 g of II was obtained 8.75 g of II-Rh.

EXAMPLE 4C

Preparation of ruthenium impregnated I (I-Ru).

Hydrated $RuCl_3$ (2 g) were suspended in acetonitrile (20 ml) and treated with neat trifluoromethane sulfonic acid (10 ml) and heated to reflux for two hours. The red solution was cooled to room temperature and filtered. The filtrate was diluted with 50 ml acetonitrile and I (10 g) was suspended therein. The suspension was left overnight with gentle stirring. The supernatant solution had changed in color to bright orange, while the polymer had turned orange.

The polymer was filtered off, washed with acetonitrile and dried in the air. Weight: 10.57 g.

EXAMPLE 4D

Preparation of palladium impregnated I (I-Pd).

$PdCl_2$ (0.18 g) was dissolved in 100 ml boiling acetonitrile. The polymer I (2 g) was added together with 20 ml of toluene. The temperature was raised to the boiling point and the volume diminished by distillation. When the volume was approximately 25 ml, the slurry was filtered. The polymer (now red) was washed with boiling acetonitrile (25 ml), boiling toluene (25 ml) and once again with boiling acetonitrile (50 ml) and air dried. Weight: 2.10 g.

EXAMPLE 4E

Preparation of platinum impregnated I (I-Pt).

$PtI_2$ (0.45 g) was refluxed with benzonitrile (50 ml) for 2 hours. The solution was cooled to room temperature and filtered. To the filtrate was added I (2 g) and the slurry was heated to reflux for 10 minutes and again cooled to room temperature. The polymer was filtered, washed with boiling acetonitrile (25 ml), boiling toluene (25 ml) and once again with hot acetonitrile (25 ml). The red material was dried in the air for several hours. Weight: 2.31 g.

Examples of Catalytic Activity of the Metal Impregnated Materials

EXAMPLE 5

Methanol carbonylation with I-Rh and II-Rh.

In a typical experiment, a laboratory scale reactor (150 ml) was loaded with methanol, methyl acetate, water, methyl iodide and I-Rh or II-Rh according to the table. The reactor contents were flushed with CO, the reactor was sealed, pressurized to 10 bar with CO, heated to the reaction temperature (185° C.) and then connected to a CO-reservoir, increasing the pressure to 35 bar. The CO-reservoir allows for the reaction to be followed continuously, giving a precise rate measurement in terms of the rate of CO consumption. After 0.5–4 hours the autoclave was cooled and depressurized. By the impregnation procedure described above, some unbound rhodium becomes absorbed in the polymer. This was washed out by submitting the material to three consecutive catalytical runs after which of each the polymer was filtered off, washed with methanol and dried (total run time was in each case 10–14 hours). The Turn-Over-Frequencies (TOF) given in Table 1 as the number of moles CO consumer pr kilogram of catalyst per hour are recorded for this pretreated catalyst.

TABLE 1

| Catalyst | Methyl iodide | Methyl acetate | Acetic acid | Water | TOF (mol kg-1 hr-1) |
| --- | --- | --- | --- | --- | --- |
| 4.0 g I-Rh | 7.28 g | 20 g | 10 g | 6 g | 51 |
| 3.8 g I-Rh | 0.83 g | 20 g | 15 g | 6 g | 6 |
| 4.2 g II-Rh | 0.75 g | 20 g | 15 g | 6 g | 7 |

A pressure other than 35 bar may be used.

EXAMPLE 6

Hydrodesulphurization and hydrogenation with I-Rh (H) and I-Ru (H).

For hydrodesulfurization, I-Rh was pretreated the following way: A reactor was loaded with 10 g I-Rh and 50 ml of toluene. The reactor was flushed with $H_2$, sealed, heated to 180° C., pressurized to 30 bar with $H_2$ and left for 20 hours. After cooling, the hydrogenated catalyst (I-Rh (H)) was filtered off and dried in a stream of hydrogen. I-Ru(H) was prepared likewise.

In a typical experiment, a plug-flow reactor was loaded with the catalyst, the system evacuated and refilled with hydrogen and heated to the relevant temperature in a steady flow of feed at the rate of 0.5 ml/min in a stream of $H_2$ at 250 ml/min and a pressure of 30 bar. The feed composition was 3% dibenzo-thiophene (DBT), 1.5% benzo-thiophene (BT) and 1% naphtalene (NAP) in n-heptane. By on-line gas chromatography, the concentration of substrate and conversion products were measured every second hour. The amount of catalyst and the conversions are to be found in Table 2.

TABLE 2

| Example No. | Catalyst type and amount | Temperature | DBT-conversion | BT-conversion | NAP-conversion |
| --- | --- | --- | --- | --- | --- |
| 1 | 0.30 g I-Rh (H) | 157° C. | 0.0% | 4.6% | 0.0% |
| 2 | 0.30 g I-Rh (H) | 177° C. | 0.0% | 6.9% | 0.0% |
| 3 | 0.30 g I | 157° C. | 0.0% | 0.0% | 0.0% |
| 4 (initial rate) | 0.30 g I-Ru (H) | 158° C. | 23.3% | 80.6% | 15.7% |
| 4 (after 12.8 hrs) | 0.30 g I-Ru (H) | 158° C. | 9.3% | 26.6% | 4.4% |

A pressure other than 30 bar may be used.

EXAMPLE 7

Hydroformylation of 1-heptene with I-Rh.

In a typical experiment, a laboratory scale reactor (150 ml) were loaded with toluene (20 g), 1-heptene (2 g) and I-Rh according to the Table. The mixture was flushed with CO, the reactor was sealed and heated to the reaction temperature (100° C.). The reactor was then connected to a gas reservoir composed of a mixture of CO and $H_2$ in equal partial pressures, and the total pressure in the reactor was adjusted to 30 bar. The temperature and pressure were held constant for 2 hours, whereafter the reactor was cooled and depressurized. The catalyst was filtered off and the contents were analyzed by GC-MS and the conversion and n/iso ratio were calculated from these data.

TABLE 3

| Example No | I-Rh | Heptenes | 1-octanal | 2-methyl-heptanal | 2-ethyl-hexanal |
| --- | --- | --- | --- | --- | --- |
| 1 | 0.50 g | 38% | 16% | 20% | 14% |

A pressure other than 30 bar may be used.

The novel acylating agent used herein, 1,1,1-tris(halomethyl)acetyl trifluoromethanesulphonate, may be used to acylate aromatic compounds other than the polymers above disclosed. The preparation of this agent and a typical use thereof is shown in the following scheme.

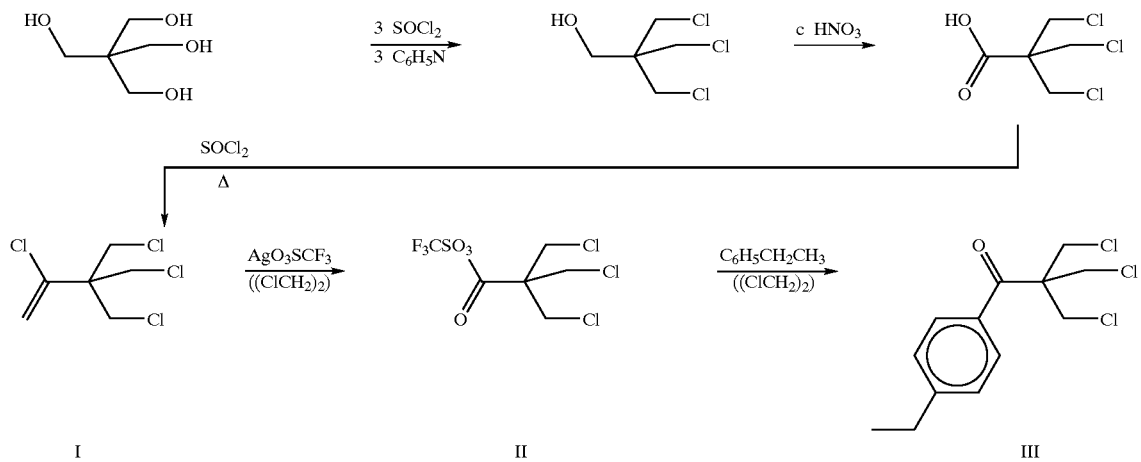

I II III

The synthesis of tris(chloromethyl)acetyl chloride ((ClCH$_2$)$_3$CCOCl) from pentaerythrithol is described in the literature (A. Mooradian and J. B. Cloke, J. Chem. Soc. 67, 942, 1945). $^1$H-NMR and $^{13}$C-NMR spectra were recorded for all intermediates and found to be in accordance with the proposed structures.

The following examples are illustrative:

EXAMPLE 8

Preparation of 1,1,1-tris(chloromethyl)acetyl trifluoromethanesulphonate.

Tris(chloromethyl)acetyl chloride (ClCH$_2$)$_3$CCOCl (56 g; 0.25 mol) were dissolved in 1,2-dichloroethane (200 ml) and stirred magnetically with solid silver trifluoromethanesulfonate (64.25 g; 0.25 mole) at room temperature for 24 hours in a dry atmosphere in the dark. This caused the formation of an almost quantitative precipitate of silver chloride, which was filtered off in a dry atmosphere and with dry equipment. The filtrate-containing the mixed carboxylic acid-trifluoromethanesulphonic acid anhydride was used immediately for acylation reactions.

EXAMPLE 9

Preparation of III and IV.

To the filtrate was added ethyl benzene (66 ml; 0.27 mole) and the mixture was refluxed 1.5 for 4 hours in the dark and in a dry atmosphere. The solution was cooled to room temperature and washed consecutively with aqueous sodium hydrogen carbonate, water and brine. The solvent was evaporated on a rotary evaporator, leaving a brown oil. This was redissolved in dichloromethane (100 ml) and decolorized by running through a short column of silica gel (4×10 cm). The column was eluded with a further 300 ml dichloromethane and all the fractions combined. After removal of the solvent, the raw product was dissolved in 300 ml boiling petrol either (60–80° C.) and cooled to –180° C. overnight causing the crystallization of the product III. By this procedure, a yield of 41, 9 g (57% based on I) of pure III was obtained. The structure was identified by 1H- and $^{13}$C-NMR spectros copy.

The mother liquor contained some additional III, but mainly the ortho-isomer 2-ethyl-(1,1,1-tris(chloromethyl) acetyl benzene IV, which was identified spectroscopically. The reaction produces the para-isomers and ortho-isomers in a ratio of approximately 2:1.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A compound having the formula CF$_3$SO$_3$C(O)C(CH$_2$X)$_3$, where X is a halogen.

2. The compound of claim 1, where X is selected from the group consisting of chlorine, bromine and iodine.

3. The compound of claim 1, where X is chlorine.

* * * * *